United States Patent
Mirzabekov et al.

[11] Patent Number: 5,908,745
[45] Date of Patent: Jun. 1, 1999

[54] USE OF CONTINUOUS/CONTIGUOUS STACKING HYBRIDIZATION AS A DIAGNOSTIC TOOL

[75] Inventors: Andrei Darievich Mirzabekov, Moscow; Gennadiy Moseyevich Yershov, Zelenograd; Eugene Vladislavovich Kirillov, Moscow; Sergei Valeryevich Parinov, Moscow; Victor Evgenievich Barski, Moscow; Yuri Petrovich Lysov, Moscow, all of Russian Federation

[73] Assignee: University of Chicago, Chicago, Ill.

[21] Appl. No.: 08/587,332

[22] Filed: Jan. 16, 1996

[51] Int. Cl.[6] .................................................. C12Q 1/68
[52] U.S. Cl. ................................................. 435/6; 436/94
[58] Field of Search .............................. 435/6; 536/22.1, 536/25.32, 26.6, 26.74; 436/94

[56] References Cited

U.S. PATENT DOCUMENTS

| | | | |
|---|---|---|---|
| 5,403,708 | 4/1995 | Brennan | 435/6 |
| 5,627,032 | 5/1997 | Ulanovsky | 435/6 |

FOREIGN PATENT DOCUMENTS

| | | | |
|---|---|---|---|
| 0535242 A1 | 3/1992 | European Pat. Off. | C12Q 1/68 |
| 89/10977 | 11/1989 | WIPO | C12Q 1/68 |

OTHER PUBLICATIONS

Khrapko, K.R. et al. "J. DNA Sequencing and Mapping, vol. 1 pp. 375–388. (1991, Harwood Academic Publishers, U.K.).

*Primary Examiner*—Kenneth R. Horlick
*Attorney, Agent, or Firm*—Cherskov & Flaynik

[57] ABSTRACT

A method for detecting disease-associated alleles in patient genetic material is provided whereby a first group of oligonucleotide molecules, synthesized to compliment base sequences of the disease associated alleles is immobilized on a predetermined position on a substrate, and then contacted with patient genetic material to form duplexes. The duplexes are then contacted with a second group of oligonucleotide molecules which are synthesized to extend the predetermined length of the oligonucleotide molecules of the first group, and where each of the oligonucleotide molecules of the second group are tagged and either incorporate universal bases or a mixture of guanine, cytosine, thymine, and adenine, or complementary nucleotide strands that are tagged with a different fluorochrome which radiates light at a predetermined wavelength. The treated substrate is then washed and the light patterns radiating therefrom are compared with predetermined light patterns of various diseases that were prepared on identical substrates.

20 Claims, 3 Drawing Sheets

Hybridized 21-mer
5'-TGGGCAGGTTGGTATCAAGGT-3'
3'-gel-CCGTCCAA-5'

-1.

1.  3'-gel-CGTCCAAC*CATAĜTTCCA*-5*
                        t 2.  3'-gel-GTCCAAC<u>C</u>-5'
                  t 3.  3'-gel-TCCAA<u>C</u>CA-5'
                t 4.  3'-gel-CCAA<u>C</u>CAT-5'

5.  3'-gel-CAACCATA-5'

+1. 3'-gel-AACCATAG*TTCCA*-5'

*ITALIC*-pentamers
\*-HEX
^-FAM

*Fig. 5*

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 22 bases
      (B) TYPE: nucleic acid
      (C) STRANDEDNESS: Not Applicable
      (D) TOPOLOGY: linear (ii) MOLECULE TYPE: Genomic DNA (ix) FEATURE:
      (A) NAME/KEY: Primer #12005
      (B) LOCATION: 1-22
      (C) IDENTIFICATION METHOD: Primer of exons to a-thalassemia
                                 gene.
      (D) OTHER INFORMATION: None (xi) SEQUENCE DESCRIPTION: SEQ ID NO: 1:

TGCCAGAAGA  GCCAAGGACA  GG                                              22

(2) INFORMATION FOR SEQ ID NO: 2:

(i) SEQUENCE CHARACTERISTICS:
      (A) LENGTH: 20 bases
      (B) TYPE: nucleic acid
      (C) STRANDEDNESS: Not Applicable
      (D) TOPOLOGY: linear (ii) MOLECULE TYPE: Genomic DNA (ix) FEATURE:
      (A) NAME/KEY: Primer # 12406
      (B) LOCATION: 1-20
      (C) IDENTIFICATION METHOD: Primer of exons to a-thalassemia
                                 gene.
      (D) OTHER INFORMATION: None.

(xi) SEQUENCE DESCRIPTION: SEQ ID NO: 2:

TAAGGGTGGG  AAAATAGACC                                                  20

(2) INFORMATION FOR SEQ ID NO: 3:

(i) SEQUENCE CHARACTERISTICS:
      (A) LENGTH: 20 bases
      (B) TYPE: nucleic acid
      (C) STRANDEDNESS: Not Applicable
      (D) TOPOLOGY: linear (ii) MOLECULE TYPE: Genomic DNA (ix) FEATURE:
      (A) NAME/KEY:  Primer # 12156
      (B) LOCATION: 1-20
      (C) IDENTIFICATION METHOD: Similarity with known sequences.
      (D) OTHER INFORMATION: Primer of exons to a-thalassemia gene.

(xi) SEQUENCE DESCRIPTION: SEQ ID NO: 3:

CATTTGCTTC  TGACACAACT                                                  20

(2) INFORMATION FOR SEQ ID NO: 4:

(i) SEQUENCE CHARACTERISTICS:
      (A) LENGTH: 19 bases
      (B) TYPE: nucleic acid
      (C) STRANDEDNESS: Not Applicable
      (D) TOPOLOGY: linear

```
    (ii) MOLECULE TYPE: Genomic DNA (ix) FEATURE:
         (A) NAME/KEY: Primer # 12313
         (B) LOCATION: 1-19
         (C) IDENTIFICATION METHOD:   Similarity with known sequences.
         (D) OTHER INFORMATION: Primer of exons to a-thalassemia gene.

(xi) SEQUENCE DESCRIPTION: SEQ ID NO: 4:

TCTCCTTAAA  CCTGTCTTG                                                    19

(2) INFORMATION FOR SEQ ID NO: 5:

(i) SEQUENCE CHARACTERISTICS:
        (A) LENGTH: 10 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
         (A) NAME/KEY: Primer # 12272
         (B) LOCATION: 1-10
         (C) IDENTIFICATION METHOD:   Similarity with known sequences.
         (D) OTHER INFORMATION: Nested primer of exons to a-thalassemia
               gene.

(xi) SEQUENCE DESCRIPTION: SEQ ID NO: 5:

CCCTGGGCAG                                                               10

(2) INFORMATION FOR SEQ ID NO: 6:

(i) SEQUENCE CHARACTERISTICS:
        (A) LENGTH: 15 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
         (A) NAME/KEY: Primer # 12299
         (B) LOCATION: 1-15
         (C) IDENTIFICATION METHOD:   Similarity with known sequences.
         (D) OTHER INFORMATION: Nested primer of exons to a-thalassemia
               gene.

(xi) SEQUENCE DESCRIPTION: SEQ ID NO: 6:

GTCTTGTAAC  CTTGG                                                        15

(2) INFORMATION FOR SEQ ID NO: 7:

(i) SEQUENCE CHARACTERISTICS:
        (A) LENGTH: 8 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
         (A) NAME/KEY: None
         (B) LOCATION: 1-8
         (C) IDENTIFICATION METHOD:   Similarity with known sequences.
         (D) OTHER INFORMATION: None.

(xi) SEQUENCE DESCRIPTION: SEQ ID NO: 7:

GGACCCGT                                                                  8

(2) INFORMATION FOR SEQ ID NO: 8:
```

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-8
            (C) IDENTIFICATION METHOD:    Similarity with known sequences.
            (D) OTHER INFORMATION: None.

(xi) SEQUENCE DESCRIPTION: SEQ ID NO: 8:

GACCCGTC                                                                          8

(2) INFORMATION FOR SEQ ID NO: 9:

(i) SEQUENCE CHARACTERISTICS:
            (A) LENGTH: 19 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-19
            (C) IDENTIFICATION METHOD:    Similarity with known sequences.
            (D) OTHER INFORMATION: None.

(xi) SEQUENCE DESCRIPTION: SEQ ID NO: 9:

CCTGGGCAGG   TTGGTATCA                                                           19

(2) INFORMATION FOR SEQ ID NO: 10:

(i) SEQUENCE CHARACTERISTICS:
            (A) LENGTH: 5 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-5
            (C) IDENTIFICATION METHOD:    Similarity with known sequences.
            (D) OTHER INFORMATION: None.

(xi) SEQUENCE DESCRIPTION: SEQ ID NO: 10:

CCAAC                                                                             5

(2) INFORMATION FOR SEQ ID NO: 11:

(i) SEQUENCE CHARACTERISTICS:
            (A) LENGTH: 5 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-5
            (C) IDENTIFICATION METHOD: Similarity with known sequences.
            (D) OTHER INFORMATION: Nested primer of exons to a-thalassemia
                gene.

(xi) SEQUENCE DESCRIPTION: SEQ ID NO: 11:

```
CGAAC                                                                            5

(2) INFORMATION FOR SEQ ID NO: 12:

(i) SEQUENCE CHARACTERISTICS:
        (A) LENGTH: 5 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
        (A) NAME/KEY: None
        (B) LOCATION: 1-5
        (C) IDENTIFICATION METHOD:    Similarity with known sequences.
        (D) OTHER INFORMATION: None.

(xi) SEQUENCE DESCRIPTION: SEQ ID NO: 12:

CAACC                                                                            5

(2) INFORMATION FOR SEQ ID NO: 13:

(i) SEQUENCE CHARACTERISTICS:
        (A) LENGTH: 5 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
        (A) NAME/KEY: None
        (B) LOCATION: 1-5
        (C) IDENTIFICATION METHOD:    Similarity with known sequences.
        (D) OTHER INFORMATION:  None.

(xi) SEQUENCE DESCRIPTION: SEQ ID NO: 13:

AAACC                                                                            5

(2) INFORMATION FOR SEQ ID NO:14:

(i) SEQUENCE CHARACTERISTICS:
        (A) LENGTH: 18 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
        (A) NAME/KEY: None
        (B) LOCATION: 1-18
        (C) IDENTIFICATION METHOD:    Similarity with known sequences.
        (D) OTHER INFORMATION:  None.

(xi) SEQUENCE DESCRIPTION: SEQ ID NO: 14:

CGTCCAACCA  TAGTTCCA                                                            18

(2) INFORMATION FOR SEQ ID NO: 15:

(i) SEQUENCE CHARACTERISTICS:
        (A) LENGTH: 8 bases
        (B) TYPE:  nucleic acid
        (C) STRANDEDNESS: Not Applicable
        (D) TOPOLOGY: linear (ii) MOLECULE TYPE: Genomic DNA (ix) FEATURE:
        (A) NAME/KEY: None
        (B) LOCATION: 1-8
```

```
            (C) IDENTIFICATION METHOD:    Similarity with known sequences.
            (D) OTHER INFORMATION:  None.

(xi) SEQUENCE DESCRIPTION: SEQ ID NO: 15:

GTCCAACC                                                                       8

(2) INFORMATION FOR SEQ ID NO: 16:

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-8
            (C) IDENTIFICATION METHOD:    Similarity with known sequences.
            (D) OTHER INFORMATION:  None.

(xi) SEQUENCE DESCRIPTION: SEQ ID NO: 16:

TCCAACCA                                                                       8

(2) INFORMATION FOR SEQ ID NO: 17:

(i) SEQUENCE CHARACTERISTICS:
            (A) LENGTH: 21 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-21
            (C) IDENTIFICATION METHOD:    Similarity with known sequences.
            (D) OTHER INFORMATION:  None.

(xi) SEQUENCE DESCRIPTION: SEQ ID NO: 17:

TGGGCAGGTT   GGTATCAAGG   T                                                   21

(2) INFORMATION FOR SEQ ID NO: 18:

(i) SEQUENCE CHARACTERISTICS:
            (A) LENGTH: 8 bases
            (B) TYPE:  nucleic acid
            (C) STRANDEDNESS: Not Applicable
            (D) TOPOLOGY: linear (ii) MOLECULE TYPE: Genomic DNA (ix) FEATURE:
            (A) NAME/KEY: None
            (B) LOCATION: 1-8
            (C) IDENTIFICATION METHOD:    Similarity with known sequences.
            (D) OTHER INFORMATION:  None.

(xi) SEQUENCE DESCRIPTION: SEQ ID NO: 18:

CCGTCCAA                                                                       8

(2) INFORMATION FOR SEQ ID NO: 19:

(i) SEQUENCE CHARACTERISTICS:
            (A) LENGTH: 13 bases
            (B) TYPE:  nucleic acid
            (C) STRANDEDNESS: Not Applicable
            (D) TOPOLOGY: linear (ii) MOLECULE TYPE: Genomic DNA
```

-continued

```
    (ix) FEATURE:
         (A) NAME/KEY: None
         (B) LOCATION: 1-13
         (C) IDENTIFICATION METHOD:    Similarity with known sequences.
         (D) OTHER INFORMATION:   None.

(xi) SEQUENCE DESCRIPTION: SEQ ID NO: 19:

AACCATAGTT  CCA                                                              13

(2) INFORMATION FOR SEQ ID NO: 20:

(i) SEQUENCE CHARACTERISTICS:
         (A) LENGTH: 8 bases
         (B) TYPE:  nucleic acid
         (C) STRANDEDNESS: Not Applicable
         (D) TOPOLOGY: linear (ii) MOLECULE TYPE: Genomic DNA (ix) FEATURE:
         (A) NAME/KEY: None
         (B) LOCATION: 1-8
         (C) IDENTIFICATION METHOD:    Similarity with known sequences.
         (D) OTHER INFORMATION:   None.

(xi) SEQUENCE DESCRIPTION: SEQ ID NO: 20:

CCAACCAT                                                                      8

(2) INFORMATION FOR SEQ ID NO: 21:

(i) SEQUENCE CHARACTERISTICS:
         (A) LENGTH: 9 bases
         (B) TYPE:  nucleic acid
         (C) STRANDEDNESS: Not Applicable
         (D) TOPOLOGY: linear (ii) MOLECULE TYPE: Genomic DNA (ix) FEATURE:
         (A) NAME/KEY: None
         (B) LOCATION: 1-9
         (C) IDENTIFICATION METHOD:    Similarity with known sequences.
         (D) OTHER INFORMATION:   None.

(xi) SEQUENCE DESCRIPTION: SEQ ID NO: 21:

CAAACCATA                                                                     9
```

USE OF CONTINUOUS/CONTIGUOUS STACKING HYBRIDIZATION AS A DIAGNOSTIC TOOL

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method for analyzing DNA sequences and more particularly this invention relates to a method for using sequencing by hybridization with oligonucleotides associated with polyacrylamide matrices, including continuous/contiguous stacking hybridization methods, to detect disease-associated alleles.

2. Background of the Invention

Present techniques for determining the existence of disease-associated alleles in patient DNA are complex, inefficient and somewhat time consuming. This is due to the fact that technologies applied to mutation location stem from complex and other error-prone base sequencing procedures. For example, one multi-step DNA sequencing approach, the Maxam and Gilbert method, involves first labeling DNA, and then splitting the DNA with a chemical, designed to alter a specific base, to produce a set of labeled fragments. The process is repeated by cleaving additional DNA with other chemicals specific for altering different bases, to produce additional sets of labeled fragments. The multiple fragment sets then must be run side-by-side in electrophoresis gels to determine base sequences.

Another sequencing method, the dideoxy procedure, based on Sanger, et al. *Proc. Natl. Acad. Sci. USA* 74, 5463–7 (1977) first requires the combination of a chain terminator as a limiting reagent, and then the use of polymerase to generate various length molecules, said molecules later to be compared on a gel. The accompanying lengthy electrophoresis procedures further detracts from the utility of this method as a fast and efficient diagnostic tool.

A more recently developed sequencing strategy involves sequencing by hybridization on oligonucleotide microchips, or matrices, (SHOM) whereby DNA is hybridized with a complete set of oligonucleotides, which are first immobilized at fixed positions on a glass plate or polyacrylamide gel matrix. There are drawbacks to this technique, however. For instance, given that short nucleotide sequences are repeated rather frequently in long DNA molecules, the sequencing of lengthy genome strings is not feasible via SHOM.

Furthermore, the procedures for manufacturing sequencing microchips with the required, large number of immobilized oligonucleotides is not perfected. For example, if immobilized octamers are utilized to determine the positions of each of the four bases in genomic DNA, then $4^8$ or 65,536 such octamers need to be fabricated and subsequently immobilized on the gel. Also, hybridization with short oligonucleotides is affected by hairpin structures in DNA.

Yet another disadvantage in using SHOM is its ineffectiveness in discriminating perfect DNA-oligomer duplexes from mismatched ones, particularly mismatched duplexes at terminal positions. Such terminal mismatches are harder to discriminate than internal mismatches.

In a variation of SHOM, sequencing of DNA strings is facilitated via a contiguous stacking hybridization (CSH) approach, whereby the microchip, comprising a gel embedded with immobilized oligomer such as an octamer (8-mer), is hybridized first with DNA and then with a fluorescently labeled oligomer such as a pentamer (5-mer). The resulting, contiguous 13 base-long oligomer (the 5-mer in a juxtaposed position to the immobilized 8-mer) thus formed acts as a probe to the DNA region.

The efficiency of CSH is due to a more stable probe being formed when the immobilized oligomer is positioned side by side with the mobilized oligomer. This extended complimentary probe therefore results in a more stable duplex between the probe and target DNA.

As with SHOM, however, there are drawbacks with CSH. First, in addition to the 65,536 immobilized oligomers already required to produce the immobilized oligo fraction in the gel matrix (discussed supra), the number of mobile oligomers (i.e. mobile pentamers) necessary to completely read the subject DNA via CSH is also formidable. When mobile pentamers are used, for example, given the possibility of any one of four bases at any one base position on the pentamer, all variations of the pentamer ($4^5$=1,024) must be produced and hybridized with the chip. Furthermore, the microchip, containing the duplexed DNA must be contacted with all the 1,024 pentamers in separate hybridization procedures (i.e. performing 1,024 additional hybridization rounds) to fully sequence the subject DNA.

Hybridization of filter-immobilized DNA with oligonucleotides in solution also has been suggested for mutation detection. However, this approach is too cumbersome for screening all possible base changes in some genes. For example, in the case of β-thalassemia, the number of changes exceeds 100.

A need exists in the art to provide an efficient method for diagnosing disease by detecting multiple mutation sequences in patient DNA. Such a method must incorporate a minimal number of oligonucleotides and utilize a minimal number of hybridization steps. The method also must be of sufficient efficiency so as to effectively discriminate perfect duplexes from imperfect ones.

SUMMARY OF THE INVENTION

It is an object of the present invention to provide a method for detecting multiple DNA base mutations, which are specific for certain diseases, that overcomes the disadvantages of the prior art.

Yet another object of the present invention is to provide a method to sequence target DNA by hybridizing the DNA first to oligonucleotide microchips and then subjecting the resulting DNA-oligo duplex to mobile oligonucleotides. A feature of the invented method is using a minimal number of mobile oligonucleotides to extend the sequences of immobilized nucleotides which are complementary to disease-associated alleles. An advantage of the invented method is enhanced detection of the DNA-oligonucleotide duplex.

Still another object of the present invention is to provide a procedure for more accurately detecting the presence of disease-associated DNA mutations. A feature of the invention is the use of universal bases or a mixture of all four bases in oligonucleotide probe sequences. An advantage of the method is producing a more sensitive method for discriminating perfect duplexes from mismatched duplexes in SHOM procedures. Another advantage is to increase the efficiency of CSH by reducing the number of mobile oligomers and hybridization rounds.

Another object of the invented method is to provide a procedure, incorporating a minimum number of stacking hybridization steps, that can accurately determine the existence of disease-associated DNA mutations. A feature of the method is the simultaneous hybridization of patient DNA, first duplexed with immobilized DNA, with mobile oligonucleotide probes, each of said probes containing a different fluorochrome. An advantage of the invented method is to decrease the number of hybridization steps, thereby expediting the process of mutation detection.

In brief, the objects and advantages of the present invention are achieved by a method for detecting disease associated alleles in patient genetic material comprising immobilizing a first group of oligonucleotide molecules of a predetermined length on a predetermined position on a substrate, said oligonucleotide molecules synthesized to compliment base sequences of the disease associated alleles; contacting the genetic material with said first group of oligonucleotides to form duplexes; contacting the duplexes with a second group of oligonucleotide molecules, said second group of oligonucleotide molecules synthesized to extend the predetermined length of the oligonucleotide molecules of the first group, and where each of the oligonucleotide molecules of the second group are tagged with a different fluorochrome which radiates light at a predetermined wavelength; washing the contacted the duplexes; and comparing the light patterns radiating from the predetermined positions on the substrate with light patterns of various diseases prepared on identical substrates.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

A method has been developed to detect DNA mutations associated with specific diseases. The method involves hybridizing patient genetic material, such as DNA or RNA to a plurality of selected nucleotide polymers having predetermined lengths, said polymers complementary to disease-associated alleles. The existence of mutations corresponding to specific diseases are determined by comparing the resulting fluorescence intensity and or patterns with those patterns which are fingerprints for specific diseases.

A preferred method is the immobilization of each of the oligonucleotide molecules in specific array locations on a gel to form microchips. The microchips are then sequentially hybridized, with the fragment of DNA (for example PCR product or clone) from an established disease-associated, allele-containing genome, and then with mobile-phase oligonucleotides that are labeled. Each of said mobile oligonucleotides may contain different fluorochromes. After reading the fluorescent pattern, the chip is washed and then subjected to a sample derived from genomic DNA (i.e. patient provided) and the same fluorescently labeled mobile phase oligonucleotides. The now-contiguous oligomeric complex thus forms a probe to aberrant DNA regions or mutations. Hybridization patterns are then compared to determine the existence of mutations.

The invented method obviates the need for the fabrication and array placement of large numbers of immobilized oligomers. Instead, the invented protocol involves the manufacture of microchips that contain a selection of specific synthetic oligomers, having a length of between approximately 6 and 16 bases, that are immobilized on a gel. Instead of the 65,536 immobilized octamers needed to detect every base sequence in an 8-base probe, relatively fewer oligomers, from between approximately a few dozen to a few hundred, that are specific for disease-associated allele sequences, are required, depending on the number of fingerprint mutations previously noted in the aberrant gene responsible for the disease. For example, a microchip with two hundred octamers, which are manufactured to complement a known allele sequence, and which are also manufactured to partly overlap each other by three nucleotides, is utilized to cover a one thousand nucleotide-long DNA molecule, by increments of five. Patient DNA is hybridized with the microchip to localize the pentanucleotide region having a changed structure. Then, successive rounds of hybridization with labeled pentamers, corresponding to the mutations, are utilized to identify the mutation.

Figure 1:
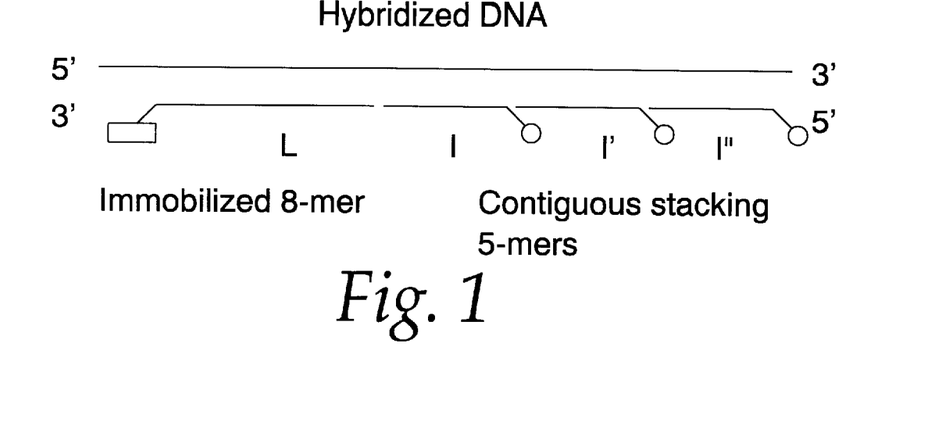
FIG. 1 is a schematic diagram of the stacking between subject matter DNA, gel-immobilized oligonucleotide sequences and oligonucleotide extending sequences, in accordance with the present invention.

FIG. 1 illustrates one embodiment of the invented stacking method. As depicted therein, an immobilized oligonucleotide of length L is hybridized with a DNA fragment. When additional oligonucleotides of length I, I' and I" are added, the duplexes formed between all of the pentamers and the DNA are stronger together than if taken separately, particularly when there is a contiguous (uninterrupted) stacking interaction between L, I, I' and I".

The inventors have found that the effective CSH interaction lengths of a microchip with immobilized octamers hybridized with one, two or three pentamers range from between 13 bases and 23 bases. Generally, a chip containing immobilized octamers is hybridized with a solution of target DNA. This is followed by several rounds of successive hybridizations with fluorescently-labeled pentamers. Thus, after the target DNA hybridizes first to the immobilized octamer, the same DNA will be available to form a duplex with one or more of the pentamers in the successive hybridization steps. Hybridization of each oligomer is detected by the fluorescence emission of the particular fluorochrome that is coupled to any one oligomer probe.

Figure 2:
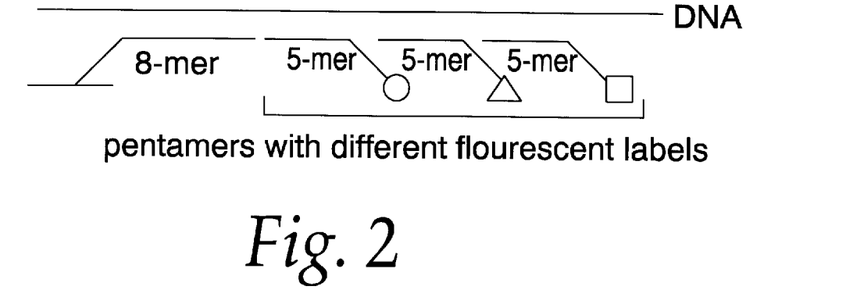
FIG. 2 is a schematic diagram of the stacking between subject matter DNA, gel-immobilized oligonucleotide sequences and a plurality of mobile oligonucleotide sequences, each mobile sequence containing a different dye, in accordance with the present invention.

In another embodiment, depicted in FIG. 2, oligonucleotides I, I' and I" are labelled with different fluorescent dyes. This allows discrimination between duplexes having lengths of for example, 8 nucleotides, 13 nucleotides, 18 nucleotides or 23 nucleotides, when immobilized oligomer fractions are 8 nucleotides long and the mobile oligomer fractions are 5 nucleotides, or multiples of 5 nucleotides long. The use of different fluorescent markers allows for simultaneous hybridization of different mobile fractions, thereby reducing the number of hybridization steps.

The invented CSH method is also applied to identify unknown base changes. In one instance, this can be accomplished if the complete set of all possible 1024 mobile pentamers is available, for example, in fragments 1,000 bases long. The first hybridization is conducted with the 200 overlapping immobilized oligomers, as discussed supra, to pin-point the region where DNA changes exist. Then, hybridization with the 1,024 mobile pentamers is conducted.

Furthermore, fewer than 1,024 hybridization steps are possible with the invented method. For example, the number of hybridization steps is decreased by a factor of four, to 256 steps (i.e. $4^4=256$), when mobile pentamers, which vary from each other in just one base position, are used.

When pentamers containing four universal bases and only one base are used, the number of hybridization steps are decreased to 20. For example, complementarity of the mobile oligomer components to the hybridized DNA is imparted by their incorporation of universal bases, such as 5-nitroindole, 3-nitropyrrole,inosine, or all four bases (the four bases being those found in DNA, namely guanine, cytosine, thymine, and adenine). As a result, successive treatment of the microchip with all possible sequences of the mobile fraction (1024 in the case of a pentamer) is obviated. As an example, for the detection of T-based localization in the DNA fragment, only five successive rounds of hybridization need be performed with pentamers of the following structure:

(first round) A-N-N-N-N-fluorochrome A;

(second round) N-A-N-N-N-fluorochrome A;

(third round) N-N-A-N-N-fluorochrome A;

(fourth round) N-N-N-A-N-fluorochrome A;and (fifth round) N-N-N-N-A-fluorochrome A;

where N designates the universal base (i.e., 5-nitroindole, 3-nitropyrrole, inosine, and an equimolar mixture of the four bases A,G,T, and C) and wherein each pentamer is labelled with the same chromophore. With all four bases to be analyzed, only 20 rounds of hybridization, instead of 1024, need to be performed.

The use of four different labels decreases the number of necessary hybridization four times more so that only 5 hybridization rounds need to be performed. In this case, at the first round of hybridization, a mixture of four probes is used with the following structure:

A-N-N-N-N-fluorochrome A;

T-N-N-N-N-fluorochrome B;

C-N-N-N-N-fluorochrome C; and

G-N-N-N-N-fluorochrome D.

The color of the resulting spot discloses the substituted base. To detect the next base, hybridization occurs with another mixture of 5-mers, as follows:

N-A-N-N-N-fluorochrome A;

N-T-N-N-N-fluorochrome B;

N-C-N-N-N-fluorochrome C; and

N-G-N-N-N-fluorochrome D.

Figure 3:
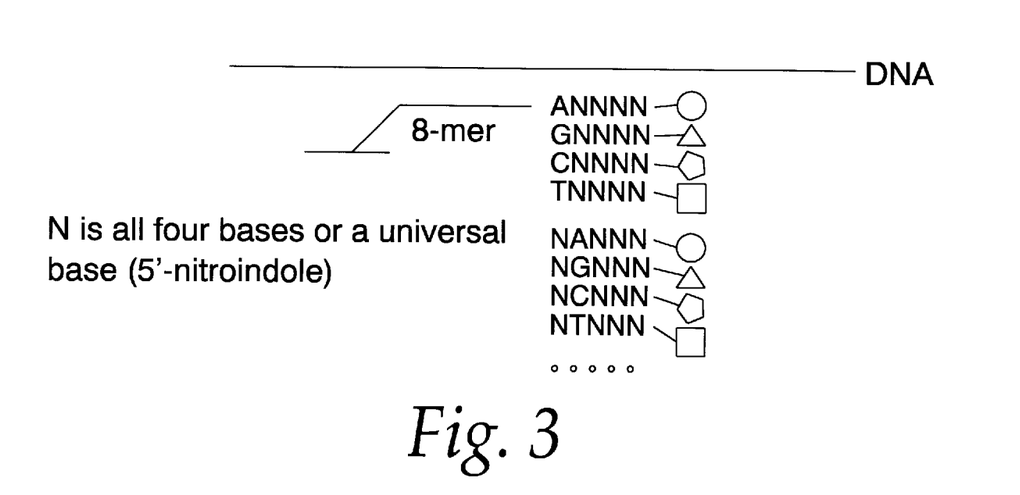
FIG. 3 is a schematic diagram of the stacking between subject matter DNA, gel-immobilized oligonucleotide sequences, and oligonucleotide extending sequences containing universal bases, or a mixture of all four bases, and different fluorochromes, in accordance with the present invention.

The third probe has an ATCG sequence at the third position, the fourth probe has an ATCG sequence at the fourth position, and the fifth probe has an ATCG sequence at the fifth position. This scenario is depicted in FIG. 3.

In addition to the use of universal base or four-base approach, different mobile oligonucleotides, among the 1024 possibilities in the case of a pentamer mobile fraction, can be labeled with different fluorochromes. In the case of two different labels, the number of hybridizations will decrease by a factor of two. In the case of four different labels, the number of required hybridizations will decrease by a factor of four. This use of different labels is illustrated in FIGS. 2 and 3 whereby the geometric shapes of a circle, triangle, pentagon and square graphically represent different tags or fluorochromes.

The resulting hybridization of genomic DNAs and pentamers to the microchips are detected using a multi-wave length fluorescence microscope coupled to a CCD-camera. Identification of the alleles present in the patient genomic DNAs are then determined by analysis of the hybridization patterns.

Microchip Manufacturing Detail

Suitable immobilization substrates must have high capacity, be relatively rigid and durable, and should be benign via hybridization. The use of gel-support for oligonucleotide immobilization offers many advantages. Oligonucleotides are tethered into the gel volume instead of being attached to the surface, thereby providing for one hundred times the capacity for immobilization (about 1 nmole/mm$^2$) than glass.

A matrix of polyacrylamide gel-elements is prepared by first polymerizing a 10–30 μm gel-layer on a glass surface. A myriad of techniques are available, including that disclosed by K. R. Khrapko et al. *J. DNA Sequencing and Mapping* Vol 1, pp.375–388, and incorporated herein by reference.

Strips of gel are then removed in perpendicular directions to yield gel squares. Each square is isolated from adjacent squares by strips of naked glass, said strips wide enough to prevent accidental mixing of oligomers. The inventors have found that widths of between approximately 80 μm and 200 μm provide good results. A scribing machine facilitates this removal, but photolithography methods are also applicable for the preparation of such gel-square elements. A laser method, developed by the inventors and disclosed in PCT/RU 92/00052, 1992, incorporated herein by reference, is also suitable.

Gel-element sizes range from approximately 40 μm×40 μm×20 μm for a micro-chip to 1 mm×1 mm×30 μm for macro-chips. Generally, chip sizes ranging from 20 μm×20 μm×20 μm to 1 mm×1 mm×30 μm produce good results. In as much as polyacrylamide gels have low fluorescent background, the sensitivity of the measurements (i.e., the ratio of signal to background) will increase with miniaturization of the gel-cell sizes, resulting in an increase in density of the DNA-oligonucleotide duplexes. The inventors were able to detect fluorescence down to 10 amol of labeled target per 100 μm×100 μm.

Oligonucleotide Synthesis Detail

The synthesis of oligonucleotides for immobilization started from 3-methyluridine, located at the 3'-end, as described in Krapko, noted supra. Oligonucleotides for hybridization were labeled with TMR either at the 3'-end by terminal transferase, provided by Promega (Madison, Wisconsin) and fluorescently labeled dUTP. Alternatively the 5' amino-group was labeled with an excess of N-hydroxysuccinimide ester of 5-carboxytetramethylrhodamine (Molecular Probe, Inc. Eugene, Oreg.) in DMSO with 50 mM sodium borate buffer, pH 9.0 at 60° C. for 30 minutes. The labeled oligonucleotides were further purified by PAGE and recovered as described in J. L. Mergny et al. *Nucleic Acid. Res.* 22, 920–928.

The synthesis of oligonucleotides containing universal bases is similar.

Oligonucleotides containing the 3-methyluridine at the 3' end were effective couplers through the aldehyde groups formed after oxidation of the 3-terminal ribose residues with sodium periodate. Prior to transfer to the gel, up to 2 nmol of oligonucleotide solution is initially oxidized in 1 mM to 10 mM $NaIO_4$ at room temperature for 10–100 minutes. Then, ethylene glycol was added to a final concentration of 50 mM. Oligonucleotides were lyophilized, dissolved in water, and then used for spotting, or alternatively, stored in the wells, 2 mm in diameter, of the teflon microliter plate, where the oxidation was initially carried out. Attachment occurs between the oxidized 3' terminal residue of the oligo and the hydrazide groups of partially modified polyacrylamide gel, whereby the gel was first activated by substituting some amide groups for hydrazide ones.

The 3-methyluridine is a good anchor in as much as it forms no stable base pairs with subject DNA.

Oligonucleotide was applied by robot onto the gel-elements in aliquots of 1 nanoliter ($10^{-9}$ liter) or more. The application technique uses a thin thermostabilised metal pin with a hydrophobic side surface and a hydrophilic end-face which determines the spotting volume. Pin temperature is kept close to the dew point to avoid evaporation of the water solution containing the oligonucleotides.

This transfer technique, developed by the applicants, is more fully disclosed in PCT/RU # 94/000180, incorporated herein by reference.

Once the micro-volumes of the solutions of the bioorganic compounds (the oligomers) have been applied to all cells of the matrix, the micro-matrix temperature is set equal to or below the dew point of the ambient air. The temperature is maintained until swelling of the gel is complete and non-coalescent droplets of water-condensate appear in the spacings between the cells. Then, a thin layer of an inert non-luminescent oil (such as NUJOR Mineral Oil from Plough, Inc.) is cautiously applied to the micro-matrix surface, the thickness of the latter layer being over 100 $\mu$m. The micromatrix is kept under the oil layer until the immobilization process is complete, preferably for at least 48 hours. The oil is then removed with a solvent, such as ethanol and water, and the matrix is dried and stored ready-for-use. More elaborate discussion of the foregoing matrix preparation procedure is found in PCT/RU94/00178, incorporated herein by reference.

The bond between an oligonucleotide and polyacrylamide is stabile enough for the matrix to withstand 10–15 rounds of hybridization without any noticeable degradation. The half-life of the oligonucleotide-gel bond at 60° C. is 2 hours, and at 25° C., 36 hours.

Oligonucleotides are immobilized on the gel in spaced arrays so as to prevent interference during hybridization and enhanced hybridization efficiencies. Gel-loading capacity limits of between 0.01 percent and 30 percent yield good results, with a preferable range of between approximately 0.1 percent and 10 percent. Concentrations of the oligo to the subject DNA can vary, and generally range from between 100 to 1,000 times higher in concentration compared to the subject DNA. Convenient subject DNA concentrations range from 0.1 to 1 picomole (pmole=$10^{-12}$ moles) in one microliter, and a typical oligo concentration is 100 micromoles (fmole=$10^{-15}$ moles) per gel element of 100 square centimeters.

It was observed that more than 70 percent of gel-immobilized oligonucleotides formed duplexes with DNA. The effective temperature stability of duplexes formed between DNA and gel-immobilized oligonucleotides depend on their concentrations and base-pair lengths. Generally, the inventors obtain good DNA complexing with immobilized oligomers at temperatures ranging from between approximately 0° C. and 60° C. Duplexing is further enhanced at high temperatures when oligonucleotides with relatively long base-pair lengths (e.g. 10-mers and 12-mers) are used. For example, when using immobilized pentamers, good duplexing occurs at between 10° C. and 20° C. When using immobilized octamers, preferable temperatures are selected from a range of between approximately 25° C. to 45° C. across the 0.01 percent to 30 percent gel capacity spectrum. This flexibility in gel loading provides the ability to equalize the stability of AT- and GC-rich duplexes in instances where universal bases are not used but where a plurality of different fluorochromes are utilized.

The inventors have found that the incorporation of additional universal bases in the mobile oligomer fraction stabilizes pentamers. Essentially, the incorporation of said universal bases turns terminal mismatches into internal mismatches, which are more easily discriminated from perfect duplex images.

Hybridization, Washing and Staining Detail

All procedures were performed on a Peltie thermotable.

Hybridization of a microchip with fluorescently labeled DNA was carried out at 0° C. for 30 minutes in 1 $\mu$l of washing buffer with 1 percent TWEEN 20 (Calbiochem, La Jolla, Calif.) detergent or any other detergent, specifically a detergent containing polyoxyethylenes. Washing buffer contained 1 M NaCl, 5 mM Na phosphate (pH 7.0), 1 mM EDTA. Thereafter 100 $\mu$l of washing buffer was pipetted on the microchip at 0° C. for 10 seconds and carefully pipetted off to remove unhybridized DNA. The washing could be repeated by varying the temperature and duration.

Contiguous stacking hybridization is carried out by hybridizing the microchip with 1 pmole of unlabeled target at 0° C. for 30 minutes, and optionally, washed at 15° C. for 2 minutes, as described, supra. The second round of hybridization was carried out with 1 $\mu$l mixture of fluorescently labeled 5-mers (5 pmol each) at 0° C. for 10 minutes. The matrix was rinsed once with washing buffer with 1 percent TWEEN 20. While a washing step is not usually necessary, any washing procedures employed usually encompassed washing off the hybridized 5-mers at 15° C. for 2 minutes, and hybridization with the other mixtures of 5-mers was repeated under the same conditions.

Fluorescence Analysis Detail

A multi-wave length fluorescence microscope coupled with a CCD-camera was assembled for image analysis. An objective yielding a 3-mm observation field enabled the simultaneous analysis of over 1,000 elements of the microchip at once. Specifically, the microscope (350 W high pressure mercury lamp, Ploem opaque with interference excitation and barrier filters for TMR) equipped with special optics and a CCD camera was built. The 3× objective with the 0.4 numerical aperture allows the illumination of the object field up to 7 mm in diameter and project 2.7×2.7 mm of the microchip on the CCD matrix. The CCD head is similar to that manufactured by Princeton Instruments (Trenton, N.J.). The exposure time varied from 0.4 to 30 seconds with a readout time of about 1.3 seconds. Variation in the sensitivity within the object area did not exceed 5 percent. The system allows operation with 1.7× objective with the same numerical aperture for analyzing 5×5 microchip areas. The instant configuration allows for rapid change-out of Filters for different fluorochromes.

The image of the microchip on the CCD camera was accommodated by a microcomputer, similar to the configuration disclosed in Khrapko, K. R. et al. *J. DNA Sequencing and Mapping*, 1, pp. 375–388, and incorporated herein by reference. For printing, linear transformation was used. This brought the highest pixel values to the same level for all images. For digital estimation, the image of the microchip element was fully covered by a 'square' twice the size of the element. Then a frame was constructed around the 'square' with equal square area. The signal of the element was calculated as the signal from the square minus the signal from the frame.

Fluorochrome Detail

Tetramethylrodamine (TMR) was used as a dye for labeling either the DNA or the mobile oligomers. Other dyes that are suitable labeling compounds include, but are not limited to, fluoresceine, Texas Red, Cascade Blue, and rhodamine, all available from Molecular Probes. HEX™, marketed by Applied Biosystems in Foster City, Calif., is another suitable dye. In the case of DNA-labeling, before measurements the microchip is incubated with fluorescent tagged DNA at 0° C. for 30 minutes and then rinsed for 10 seconds with washing buffer to remove unbound targets. Perfect duplexes are discriminated already in the process of hybridization despite rather high intensities of the fluorescence signal from the unbound target. More effective discrimination of perfect duplexes from mismatched ones are achieved by plotting the dissociation curve either at temperature gradient or at a fixed temperature while changing the duration of washing. Real-time measurements allowed for the choice of optimal conditions for discrimination when the mismatched signals are close to background levels. Temperatures are controlled by a Peltie thermotable.

PCR Detail

PCR amplifications were performed by an adapted procedure by Postnikov et al. *Hemoglobin* 17,439–453 (1993), and incorporated herein by reference. Initially, amplification of 421 bp-long product was carried out with 1 ng of genomic DNA, primers #12005 TGCCAGAAGAGCCMGGACAGG (SEQ ID NO:1) and #12406 TAAGGGTOGGCCCCTA-GACC (SEQ ID NO:2). The reaction conditions were as follows: 30 cycles with 40 seconds at 93° C., 30 seconds at 67° C. and 30 seconds at 72° C. 5 μl of the PCR were transferred to the reaction mixture for amplification with nested primers. Nesred primers, #12156 CATTTGCTTCT-GACACAACT (SEQ ID NO:3) and #12313 TCTCCT-TAAACCTGTCTTG (SEQ ID NO:4), were used to amplify 176 bp-long DNA for 25 cycles (30 seconds at 90° C., 30 seconds at 50° C., 20 seconds at 72°C.). The PCR with fluorescently nested primers (labeled #12272 CCCTGGGCAG (SEQ ID NO:5) and normal #12299 GTCTTGTAACCTTG (SEQ ID NO:6) was carried out for 25 cycles (30 seconds at 80° C., 30 seconds at 35° C.) and yielded 32 bp product. PCT was purified by PAGE or by enrichment procedures.

EXAMPLE 1

Figure 4:
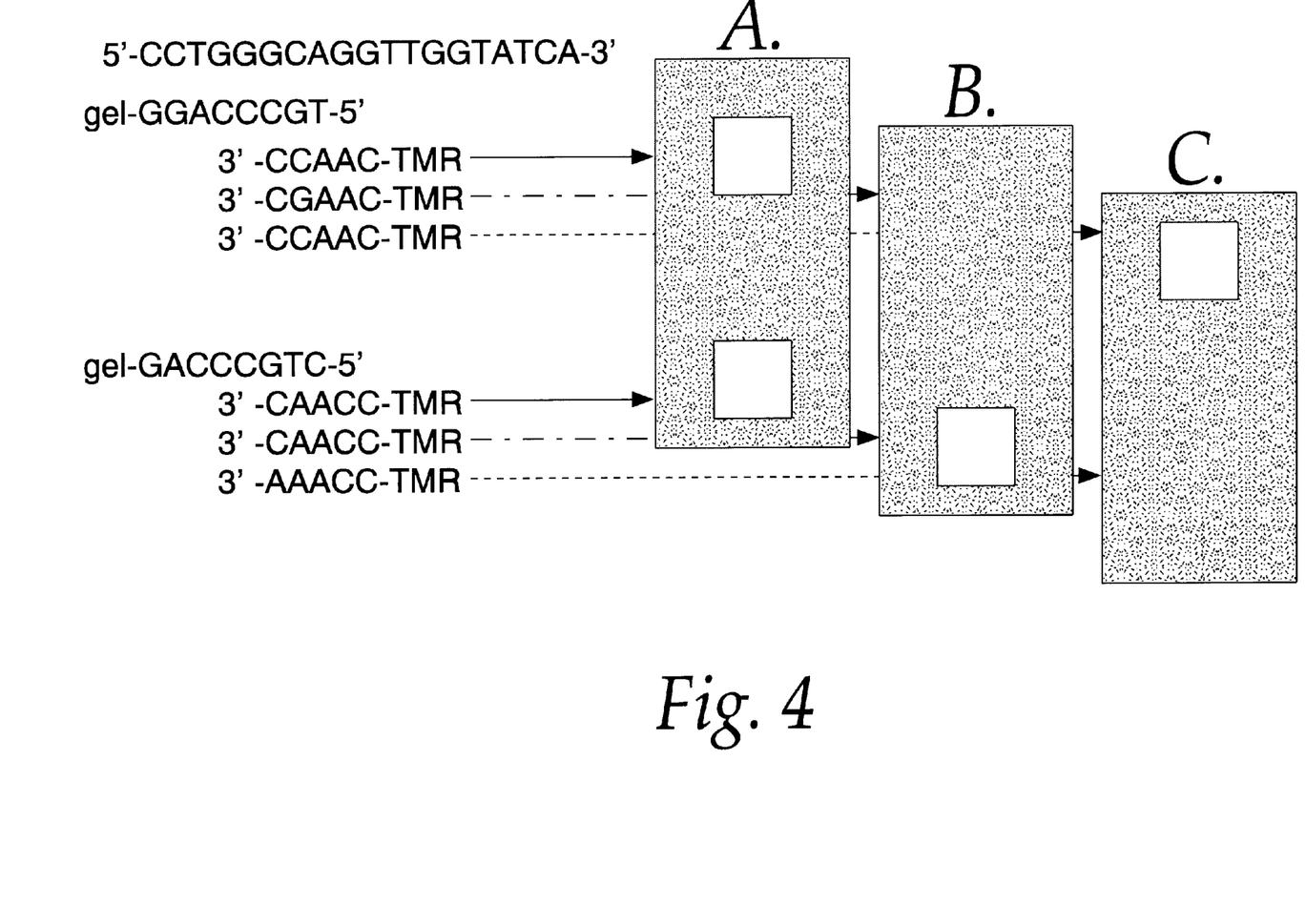
FIG. 4 is a diagram of fluorograms of specific hybridization experiments with specific immobile and mobile oligonucleotides, in accordance with the present invention.

Two 8-mers GGACCCGT (SEQ ID NO:7) and GAC-CCGTC (SEQ ID NO:8) located one and two bases away from a mutation site were immobilized on a microchip, and the microchip was hybridized to the unlabeled 19-mer CCTGGGCAGGTTGGTATCA (SEQ ID NO:9). Then the duplexes formed on the microchip were hybridized in three more rounds with pools of two labeled 5-mers CCAAC (SEQ ID NO:10), CGAAC (SEQ ID NO:11), CAACC (SEQ ID NO:12), and AAACC (SEQ ID NO:13). The results are illustrated in FIG. 4. Some hybridized pentamers formed perfect duplexes in a juxtaposed position to the immobilized 8-mer and extended it to a 13 bp-long duplex.

These 13-base perfect duplexes were stable due to stacking interactions between 5'- and 3' terminal bases of the 8-mer and 5-mer, respectively, despite lacking a phosphodiester bond. Mismatches in the internal, or even in the terminal, position destabilized the interaction of the 5-mers much more than 8-mers.

As can be noted in FIG. 4, the mismatched 5-mers were either not hybridized at all or washed out at much lower temperature than fully complementary 5-mer. Therefore, inclusion of 5-mers provided better discrimination of perfect duplexes from mismatched ones than just immobilized 8-mers, particularly in the case of terminal mismatches. The 8-mer duplexes remained stable under the washing conditions for the pentamers. The microchips sustained up to 10 rounds of successive hybridization with 5-mers. The 5-mers can also be ligated to 8-mers enzymatically. However, the ligation could complicate those experiments where several rounds of CSH are to be performed.

EXAMPLE 2

Figure 5:
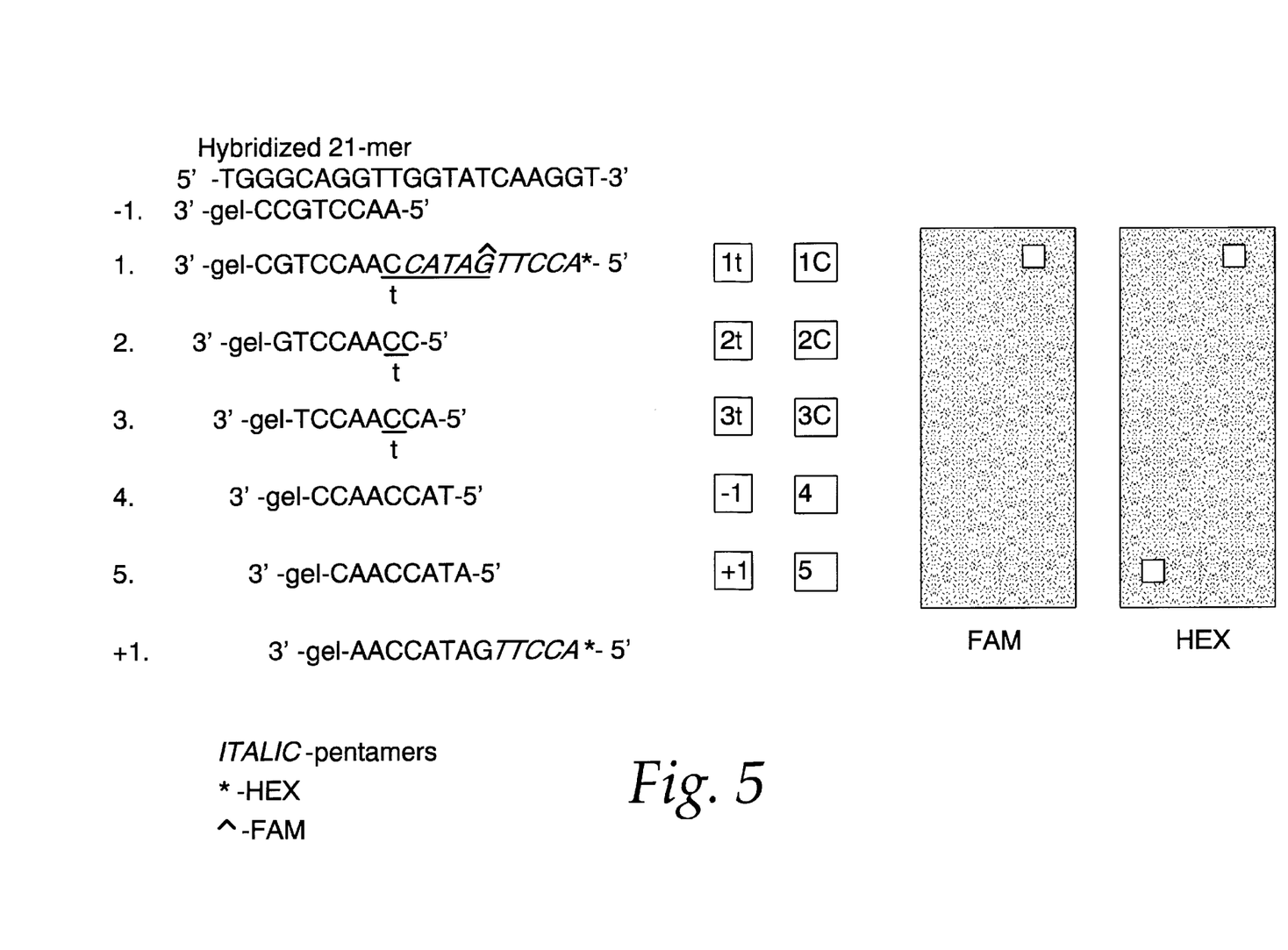
FIG. 5 is a diagram of fluorograms of specific hybridization experiments using a plurality of tags, in accordance with the present invention.

FIG. 5 depicts another embodiment wherein a plurality of tags or fluorochromes are used to detect target sequences. In this embodiment, a microchip was constructed, consisting of 10 immobilized octamers, with sequences engineered to affect a three-base overlap. For octamer sequence strings labeled "1. CGTCCAACCATAGTTCCA (SEQ ID NO:14)", "2. GTCCAACC (SEQ ID NO:15)", and "3. TCCAACCA (SEQ ID NO:16)", the sequences varied by either a cytosine or thyamine, as indicated by the underscore.

The microchip was hybridized with a 21-nucleotide-containing sequence (21-mer) TGGGCAGGTTGGTAT-CAAGGT (SEQ ID NO:17). After the hybridization procedure, unhybridized 21-mer was removed and the microchip was hybridized with a mixture of HEX-labeled pentamer ACCTT and FAM-labeled pentamer GATAC, at a labelling concentration of 50 percent of total pentamer. Detection of the HEX- and FAM-tags (designated as * and ˆ, respectively) was performed by changing to the corresponding sets of optical filters.

The octanucleotide CCGTCCA (SEQ ID NO:18) labeled as "−1." was constructed as a negative control, in as much as this string did not interact with a pentamer. Octamer "+1" AACCATAGTTCCA (SEQ ID NO:19) was constructed as a positive control for hybridization, and for proper filter function.

As can be noted in FIG. 5, the invented contiguous stacking method of using a plurality of tags provides excellent detection of target sequences, and with no false negatives or positives. For example, String "1.", depicting an immobilized octamer stacked with two mobile, and differently-labeled pentamers (in italics), clearly revealed the presence of the target sequence when each tag was utilized.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for detecting disease associated alleles in patient genetic material comprising:
   a) immobilizing oligonucleotide molecules from a first group, at a predetermined position on a substrate, each of the molecules having a first end, a second end, and a known length, whereby the first end is attached to the substrate said oligonucleotide molecules synthesized to complement base sequences of the disease associated alleles;
   b) contacting the patient genetic material with said first group of oligonucleotides to form duplexes;
   c) positioning oligonucleotide molecules from a second group of oligonucleotide molecules at the second end of the immobilized oligonucleotide molecules of the first group to noncovalently extend the length of the oligonucleotide molecules of the first group, where each of the oligonucleotide molecules of the second group are tagged with a fluorochrome which radiates light at a predetermined wavelength, and where each of the oligonucleotide molecules of the second group consist of "n" number of bases and wherein just one of the bases of the oligonucleotide molecules of the second group is guanine or cytosine or thymine or adenine or uracil with the remaining bases each comprised of a universal base selected from the group consisting of 5-nitroindole, 3-nitropyrrole, and inosine; and
   d) comparing the light patterns radiating from the predetermined positions on the substrate with predetermined light patterns emitted from identical substrates which were contacted with the disease associated alleles.

2. The method as recited in claim 1 wherein the patient genetic material are polynucleotides selected from the group consisting of deoxyribonucleic acid and ribonucleic acid.

3. The method as recited in claim 1 wherein the oligonucleotide molecules of the first group of oligonucleotides consists of different oligonucleotide sequences and are of equal length.

4. The method as recited in claim 1 wherein the length of the oligonucleotides in the first group is between 8 and 20 bases.

5. The method as recited in claim 1 wherein the oligonucleotide molecules of the second group of oligonucleotides consist of different base sequences and are of equal length.

6. The method as recited in claim 1 wherein the predetermined length of the oligonucleotides in the second group is between 4 and 7 bases.

7. The method as recited in claim 1 wherein the fluorochrome which radiates light at a predetermined wavelength is selected from the group consisting of tetramethylrodamine, fluoresceine, Texas Red, Cascade Blue, rhodamine, HEX and combinations thereof.

8. The method as recited in claim 1 wherein the oligonucleotide molecules of the second group are tagged with the same fluorochrome and step c is repeated 4n times.

9. The method as recited in claim 1 wherein the oligonucleotide molecules of the second group are tagged with different fluorochromes with each fluorochrome specific for only one of guanine or cytosine or thymine or adenine, or uracil and step c is repeated n times.

10. A method for determining nucleotide sequences from patient genetic material comprising:
  a) immobilizing oligonucleotide molecules from a first group, at a predetermined position on a substrate, each of the molecules having a first end, a second end, and a known length, whereby the first end is attached to the substrate, said oligonucleotide molecules synthesized to complement base sequences of the disease associated alleles;
  b) contacting the patient genetic material with said first group of oligonucleotides to form duplexes;
  c) positioning oligonucleotide molecules from a second group of oligonucleotide molecules at the second end of the immobilized oligonucleotide molecules of the first group to noncovalently extend the length of the oligonucleotide molecules of the first group, where each of the oligonucleotide molecules of the second group are tagged with a fluorochrome which radiates light at a predetermined wavelength, and where each of the oligonucleotide molecules of the second group consist of "n" number of bases and wherein just one of the bases of the oligonucleotide molecules of the second group is guanine or cytosine or thymine or adenine and the remaining bases are each comprised of a universal base selected from the group consisting of 5-nitroindole, 3-nitropyrrole, and inosine; and
  d) repeating step c to determine the complete sequence of the patient genetic material duplexed with both the oligonucleotide molecules from the first group and the oligonucleotide molecules from the second group.

11. The method as recited in claim 10 wherein all of the nucleotide molecules of the second group contain the same fluorochrome and step c is repeated 4n times.

12. The method as recited in claim 11 wherein the number of nucleotide molecules in the second group is 4n.

13. The method as recited in claim 10 wherein the fluorochrome is specific for only one of guanine or cytosine or thymine or adenine and step c is repeated n times.

14. The method as recited in claim 13 wherein the number of nucleotide molecules in the second group is n.

15. A method for determining nucleotide sequences from patient genetic material comprising:
  a) immobilizing oligonucleotide molecules from a first group, at a predetermined position on a substrate, each of the molecules having a first end, a second end, and a known length, whereby the first end is attached to the substrate, said nucleotide molecules synthesized to complement base sequences of the disease associated alleles;
  b) contacting the patient genetic material with said first group of oligonucleotides to form duplexes;
  c) positioning oligonucleotide molecules from a second group of oligonucleotide molecules at the second end of the immobilized oligonucleotide molecules of the first group to noncovalently extend the length of the oligonucleotide molecules of the first group, where each of the oligonucleotide molecules of the second group are tagged with a fluorochrome which radiates light at a predetermined wavelength, and where each of the oligonucleotide molecules of the second group is a pentamer containing four universal bases and just one base is guanine or cytosine or thymine or adenine; and
  d) repeating step c to determine the base sequence of the patient genetic material that extends five bases beyond the second end of the immobilized oligonucleotide molecule.

16. The method as recited in claim 15 wherein the universal base is 5-nitroindole, 3-nitropyrrole or inosine.

17. The method as recited in claim 15 wherein the second group of oligonucleotide molecules consist of five subgroups with the first subgroup consisting of
  A-N-N-N-N, T-N-N-N-N, C-N-N-N-N, and G-N-N-N-N, the second group consisting of
  N-A-N-N-N, N-T-N-N-N, N-C-N-N-N, and N-G-N-N-N, the third group consisting of
  N-N-A-N-N, N-N-T-N-N, N-N-C-N-N, and N-N-G-N-N, the fourth group consisting of
  N-N-N-A-N, N-N-N-T-N, N-N-N-C-N, and N-N-N-G-N, and the fifth group consisting of
  N-N-N-N-A, N-N-N-N-T, N-N-N-N-C, and N-N-N-N-G
  where N is the universal base, A is adenine, T is thymine, C is cytosine and G is guanine.

18. The method as recited in claim 17 wherein each of the molecules in each of the subgroups are tagged with a fluorochrome specific for only one of guanine, or cytosine or thymine or adenine and only one subgroup at a time is positioned at the second end of the immobilized oligonucleotide molecules.

19. The method as recited in claim 15 wherein the pentamers are derived from five structures, the first structure consisting of
  X-N-N-N-N, the second structure consisting of
  N-X-N-N-N, the third structure consisting of
  N-N-X-N-N, the fourth structure consisting of
  N-N-N-X-N, and the fifth structure consisting of
  N-N-N-N-X,
wherein N designates the universal base, X designates the same base, each of the five structures contain the same fluorochrome that is specific for that base, and only one structure at a time is positioned at the second end of the immobilized oligonucleotide molecules.

20. The method as recited in claim 19 wherein a different base and a fluorochrome specific for that base is utilized.

* * * * *

UNITED STATES PATENT AND TRADEMARK OFFICE
CERTIFICATE OF CORRECTION

PATENT NO. : 5,908,745
DATED : June 1, 1999
INVENTOR(S) : MIRZABEKOV et al.

It is certified that error appears in the above-indentified patent and that said Letters Patent is hereby corrected as shown below:

Column 24, line 3, after the word "said," delete "nucleotide," and insert the word --oligonucleotide--.

Signed and Sealed this

Twenty-third Day of May, 2000

Attest:

Q. TODD DICKINSON

Attesting Officer    Director of Patents and Trademarks